United States Patent [19]
Engelbrecht et al.

[11] Patent Number: 4,790,853
[45] Date of Patent: * Dec. 13, 1988

[54] KNEE JOINT PROSTHESIS

[75] Inventors: Eckart Engelbrecht; Elmar Nieder, both of Hamburg; Arnold Keller, Kayhude, all of Fed. Rep. of Germany

[73] Assignees: GMT Gesellschaft Für Medizinische Technik MBH; Waldemar Link GmbH & Co., both of Hamburg, Fed. Rep. of Germany

[*] Notice: The portion of the term of this patent subsequent to Sep. 3, 2002 has been disclaimed.

[21] Appl. No.: 769,522

[22] Filed: Aug. 26, 1985

Related U.S. Application Data

[63] Continuation-in-part of Ser. No. 398,638, Jul. 15, 1982, Pat. No. 4,538,305.

[30] Foreign Application Priority Data

Aug. 29, 1984 [DE] Fed. Rep. of Germany ....... 3431645

[51] Int. Cl.⁴ ................................................ A61F 2/38
[52] U.S. Cl. ..................................................... 623/20
[58] Field of Search ..................................... 623/16-23

[56] References Cited

U.S. PATENT DOCUMENTS 4,136,405  1/1979  Pastrick et al. ..................... 623/20
4,538,305  9/1985  Engelbrecht et al. ............... 623/18

Primary Examiner—Richard J. Apley
Assistant Examiner—David J. Isabella
Attorney, Agent, or Firm—Peter K. Kontler

[57] ABSTRACT

A knee joint prosthesis wherein a first component which is partially embedded in the femur carries a pivotably mounted tubular guide for a pin-shaped second guide mounted on a second component which is partially embedded in the tibia. The second guide is rotatable and reciprocable in the tubular guide, and the extent of the reciprocatory movement is limited by two abutments one of which is mounted on the first component and the other of which is mounted on the second component.

19 Claims, 2 Drawing Sheets

KNEE JOINT PROSTHESIS

CROSS-REFERENCE TO RELATED CASE

This is a continuation-in-part of our copending patent application Ser. No. 398,638 filed July 15, 1982 for "Articulated Prosthesis", now U.S. Pat. No. 4,538,305 granted Sept. 3, 1985.

BACKGROUND OF THE INVENTION

The present invention relates to prostheses in general, and more particularly to improvements in internal prostheses, especially those which can replace knee joints.

It is known to assemble an internal prosthesis of two components having extensions which can be embedded in the marrow cavities of bones whose joint (such as a knee joint) is to be replaced with a prosthesis. It is also known to construct a prosthesis in such a way that the two components have a freedom of movement relative to each other in the longitudinal direction of the components, e.g., to increase or reduce the distance between a femur and a tibia. In addition, in the case of a knee prosthesis the tibia can pivot relative to the femur and/or vice versa about a transverse axis and the tibia can turn relative to the femur about a second axis which is at least substantially normal to the pivot axis and extends longitudinally of the tibia. The extent to which the tibia can move longitudinally toward or away from the femur (or vice versa) is determined or is intended to be determined by the so-called soft-part apparatus to the extent that such apparatus is capable of carrying out its function. This means that the movability of the tibia relative to the femur in the longitudinal direction of the tibia can be limited only if the aforementioned apparatus is capable of performing such work. On the other hand, there exists an urgent need for highly versatile internal prostheses, e.g., for prostheses to be used in lieu of knee joints, which allow for longitudinal movements of the articulately connected bones relative to each other irrespective of the condition of that portion or those portions of the anatomy which are presently intended to control and determine the extent of such movements.

OBJECTS AND SUMMARY OF THE INVENTION

An object of the invention is to provide a novel and improved articulated prosthesis, especially an internal prosthesis, which ensures that the bones which are joined to each other can perform a variety of movements in imitation of movements which are permitted by a joint (such as a knee) even if the body of the patient is incapable of limiting certain movements of the components of the prosthesis relative to each other.

Another object of the invention is to provide a prosthesis which can be utilized as a superior substitute for highly sophisticated conventional prostheses even if the body of the user is not in a condition which would permit full utilization of conventional prostheses.

A further object of the invention is to provide a novel and improved knee prosthesis.

An additional object of the invention is to provide a prosthesis which can be utilized by persons of all age groups and which can be assembled in a simple and time-saving operation.

A further object of the invention is to provide novel and improved hinges which can be used in a prosthesis of the above outlined character.

The invention is embodied in an articulated prosthesis, particularly in an internal prosthesis, which comprises elongated first and second components arranged to engage with the respective parts of the anatomy, i.e., with the parts which are normally connected to each other by a joint which is to be replaced with the prosthesis (e.g., by a knee joint). The components are reciprocable with reference to each other in their longitudinal directions and the improved prosthesis further comprises stop means for limiting the extent of reciprocability of the two components with reference to each other. This ensures that the extent of reciprocatory movements of the first component relative to the second component and/or vice versa is not determined by the ability of the user to control or limit such movements but is determined by a portion of the prosthesis proper. For example, the first component can comprise an elongated extension which can be embedded or otherwise received in a femur, and the second component can include an elongated extension which is embedded or otherwise received in a tibia. No mechanical connection is provided between the components 1 and 2.

The prosthesis preferably further comprises a first hinge which is provided on one of the components and defines a first axis extending transversely of the corresponding part of the anatomy of the user and serving to permit relative movements of the two components about such axis, and a second hinge defining for the two components a second axis which is at least substantially normal to the first axis. The second hinge permits clockwise and counterclockwise angular movements of the two components relative to each other about the second axis. The first hinge preferably comprises a first (e.g., female) portion which is rigid with the extension of the first component and a second (e.g., male) portion which is complementary to the first portion and includes a first guide (preferably a tubular guide) which is pivotable with the second portion of the first hinge about the first axis. The second component comprises a second guide (e.g., a pin which is rotatably and reciprocably received in the first guide) which cooperates with the first guide to constitute therewith the second hinge for clockwise and counterclockwise angular movement of the two components about the second axis. One of the two components is reciprocable relative to the other component and/or vice versa in the direction of the second axis and to the extent which is determined by the stop means.

The stop means preferably comprises a first abutment which is provided on the first component and at least partially surrounds the first guide, and a second abutment provided on the second component and serving to engage the first abutment in response to movement of the one component in the direction of the second axis and away from the first component, i.e., in a direction away from the first axis. A portion of the component which carries the first abutment preferably extends into the femur and a portion of the component which carries the second abutment preferably extends into the tibia if the improved prosthesis replaces a knee joint.

The second guide is preferably rigid with the second component and the first guide preferably surrounds the second guide and is coupled to the first component for pivotal movement about the first axis. The first abutment is preferably provided on that end portion of the first guide which is remote from the first axis. One side of the first abutment faces away from the second component and is in contact with the second abutment in a predetermined end position of the one component, as considered in the direction of the second axis, in which the second component is located at a maximum distance from the first axis. The first abutment can be formed with a flat which is located at one side of the second axis and moves toward and away from the extension of the first component in response to movement of the two components relative to each other about the first axis.

The second component is preferably provided with a bearing element and with means for mounting the second abutment on the bearing element. Such mounting means can comprise a substantially plate-like and preferably horseshoe-shaped member which is affixed to the bearing element and partially surrounds the first guide. The plate-like member is located in a plane which is at least substantially normal to the second axis, and one of its sides faces toward the first component which latter is preferably provided with a second bearing element adjacent to and movable into contact with the one side of the plate-like member. The plate-like member is preferably formed with a recess bounded by a substantially U-shaped internal surface including a concave portion which is outwardly adjacent to the preferably cylindrical external surface of the first guide. The first abutment preferably includes an arcuate portion which is adjacent to the second abutment, as considered in the direction of the second axis. The second abutment preferably extends radially inwardly beyond the concave portion of the U-shaped internal surface of the plate-like member and toward the second axis. This second abutment is preferably located at one end of the concave portion of the U-shaped internal surface, as considered in the direction of the second axis, namely at that end which is nearer to the first axis. The second abutment is preferably formed with a concave surface which is complementary to the preferably cylindrical external surface of the first guide.

The bearing element of the second component can include a platform one side of which faces toward the first component, and the first abutment is disposed between such side of the platform and the second abutment. The platform and the second abutment define a space which receives the first abutment with limited freedom of movement in the direction of the second axis. In other words, the first abutment has limited freedom of movement between the bearing element of the second component and that abutment (namely the second abutment) which is mounted on the second component. The means for securing the plate-like member to the platform preferably comprises a screw or another suitable fastener whose head is at least partially recessed into the plate-like member or into the platform. The platform is preferably provided with a beaded portion which is received in a complementary groove of the plate-like member or vice versa. At any rate, the platform and the plate-like member are preferably in a pronounced surface-to-surface contact with each other. Means can be provided for releasably retaining or maintaining the platform and the plate-like member in pronounced surface-to-surface contact with each other. Such retaining means can comprise at least one socket in the platform or in the plate-like member and a coupling element (e.g., a pin or the like) which is provided on the plate-like member or on the platform and extends into the socket. Two such sockets (e.g., in the form of blind bores) can be disposed in a plane which includes the plane of the plate-like member.

The novel features which are considered as characteristic of the invention are set forth in particular in the appended claims. The improved prosthesis itself, however, both as to its construction and its mode of operation, together with additional features and advantages thereof, will be best understood upon perusal of the following detailed description of certain specific embodiments with reference to the accompanying drawing.

DESCRIPTION OF THE PREFERRED EMBODIMENTS

Figure 1:
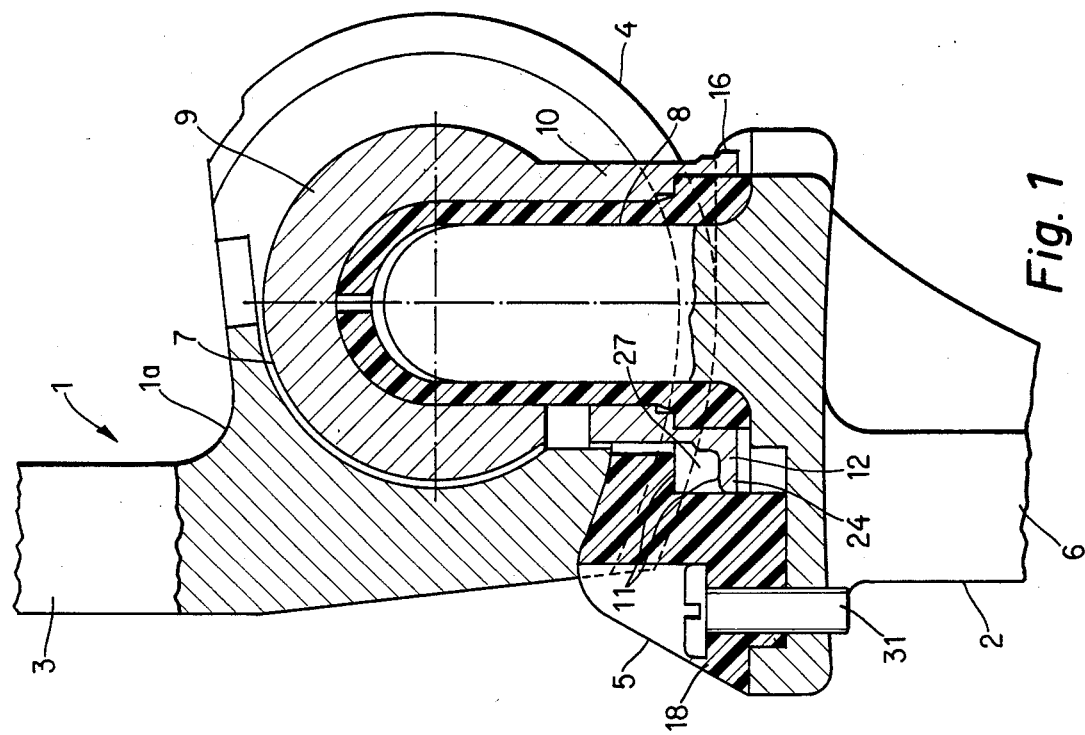
FIG. 1 is a fragmentary partly side elevational and partly vertical sectional view of a knee joint prosthesis which embodies one form of the present invention.

The illustrated articulated prosthesis is an internal prosthesis which includes a first elongated component 1 having an extension 3 which can be fitted into the marrow cavity of the adjacent femur and a second elongated component 2 having an elongated extension 6 which can be fitted into the marrow cavity of a tibia. The lower portion of the femoral component 1 constitutes a bearing element 4 which cooperates with and can rest on a complementary bearing element 5 of the tibial component 2. The prosthesis comprises a first hinge 7 which enables the components 1 and 2 to perform pivotal movements about a substantially horizontal axis A which extends substantially transversely of the longitudinal directions of the components 1 and 2 and substantially transversely of the corresponding part of the anatomy. The prosthesis further comprises a second hinge 8 which enables the components 1 and 2 to perform relative angular movements about a second axis B which is at least substantially normal to the first axis and extends longitudinally of the tibial component 2.

The first hinge 7 is a swivel joint having a part cylindrical male portion 9 which is rotatably journalled in a female portion 1a of the component 1 for movement about the axis A and has a downwardly extending tubular female guide 10 surrounding a pinshaped male guide 14 which is provided on the component 2 and is reciprocable in the guide 10 in directions which are indicated by the arrow C, i.e., in the direction of the axis B. The prosthesis further comprises stop means 11 for limiting the extent of movability (reciprocability) of the components 1 and 2 relative to each other in one of the directions which are indicated by the arrow C, namely the extent of downward movement of the component 2 and/or the extent of upward movement of the component 1, as viewed in FIG. 1 or 2. The stop means 11 comprises a first abutment 12 which is provided at the lower end of the tubular female guide 10 and a second abutment 13 which is mounted on the bearing element 5 of the component 2 and can move into engagement with the abutment 12 when the male guide 14 is caused to move downwardly, as viewed in FIG. 1 or 2. The abutment 12 is a collar shaped part which surrounds the lower end portion 15 of the female guide 10 and is overlapped by the abutment 13. The guide 10 can turn relative to the component 1 about the horizontal or transverse pivot axis A, and the guide 14 can turn relative to the guide 10 about the second axis B; at the same time, the guide 14 can move axially (arrow C) relative to the guide 10 and/or vice versa to the extent which is determined by the stop means 11 including the abutments 12 and 13. It will be noted that the abutment 12 extends radially outwardly and away from the axis B and male guide 14. The upper side of the collar-shaped abutment 12 has a substantially plane surface 17 which is contacted by the underside of the abutment 13 when the latter moves to its lower end position, as viewed in FIG. 1 or 2, i.e., when the component 2 moves longitudinally and away from the pivot axis A which is defined by the hinge 7.

Figure 2:
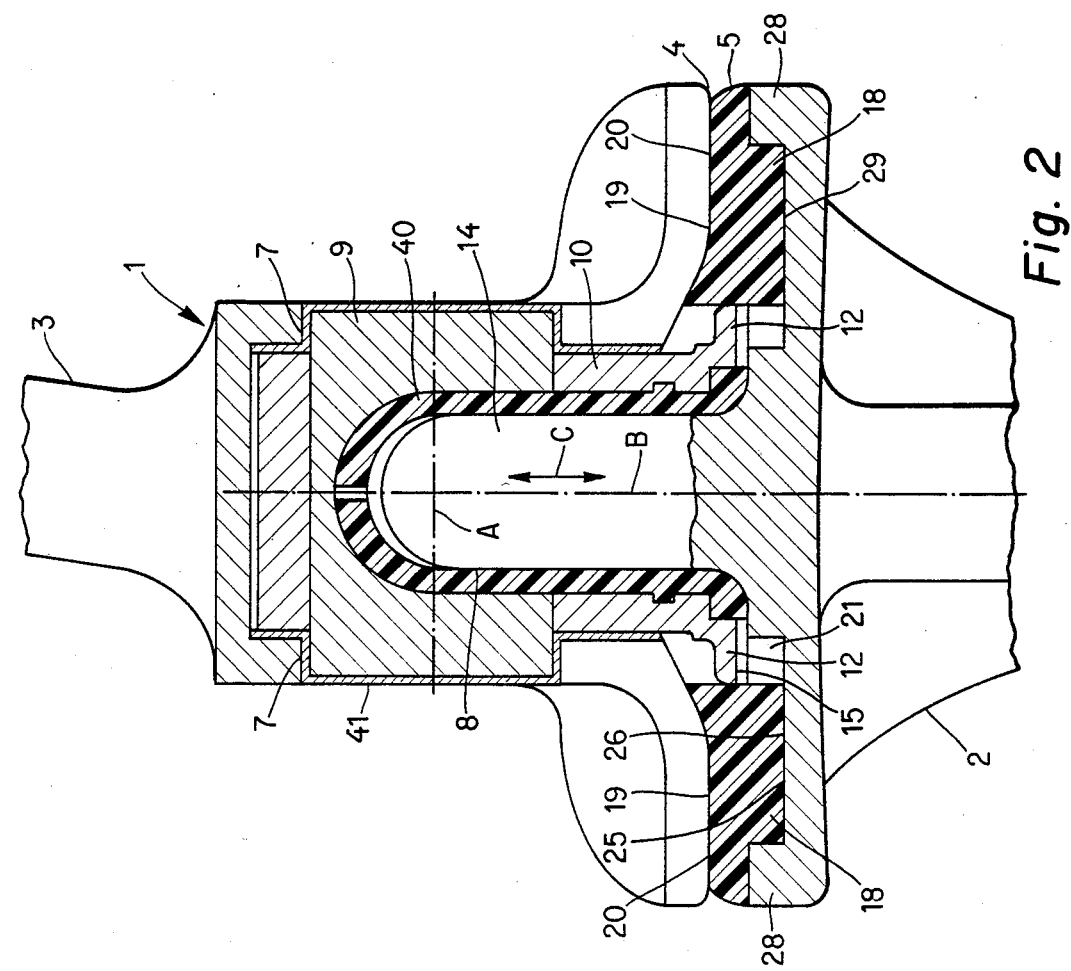
FIG. 2 is a fragmentary partly front elevational and partly vertical sectional view of the prosthesis which is shown in FIG. 1.
Figure 3:
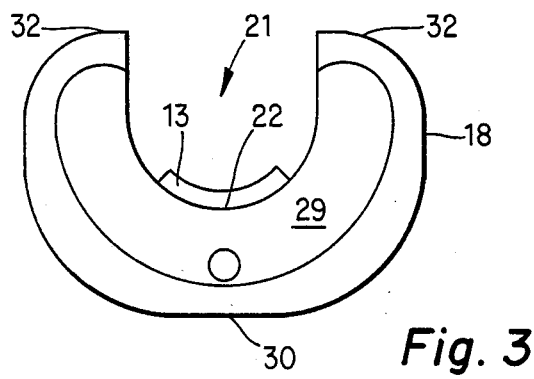
FIG. 3 is a bottom plan view of a plate-like mounting member which is mounted on the tibial component and includes one of the abutments.
Figure 4:
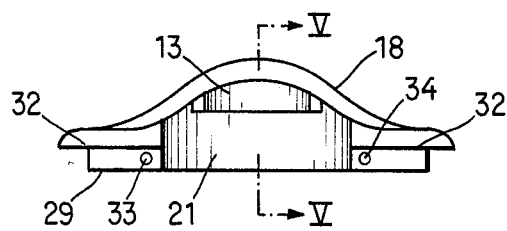
FIG. 4 is a rear elevational view of the plate-like mounting member which is shown in FIG. 3.
Figure 5:
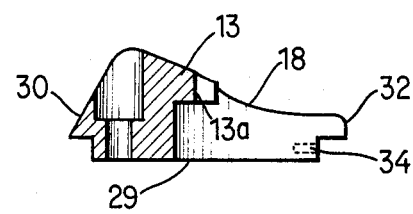
FIG. 5 is a sectional view as seen in the direction of arrows from the line V—V of FIG. 4.
Figure 6:
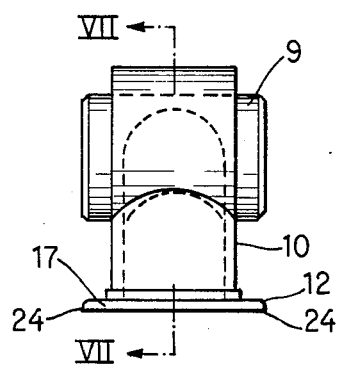
FIG. 6 is a smaller-scale fragmentary front elevational view of the guides which constitute the second hinge in the prosthesis of FIGS. 1 and 2.
Figure 7:
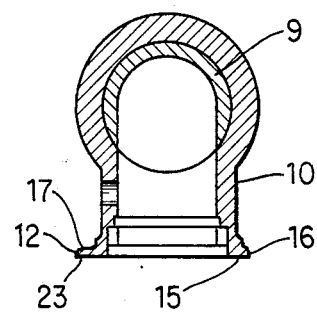
FIG. 7 is a sectional view as seen in the direction of arrows from the line VII—VII of FIG. 6.
Figure 8:
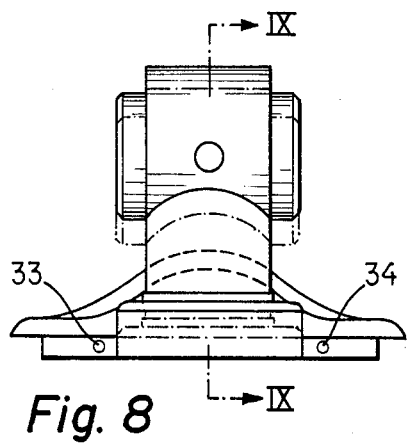
FIG. 8 is a smaller-scale rear elevational view of the two hinges and of the mounting member of FIGS. 3 to 5.
Figure 9:
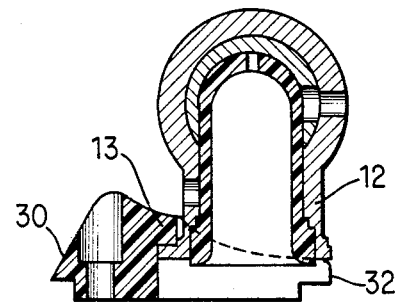
FIG. 9 is a sectional view as seen in the direction of arrows from the line IX—IX of FIG. 8.

When the user of the prosthesis bends his or her knee by pivoting the tibia in a clockwise direction (about the axis A), as viewed in FIG. 1, the bearing element 5 of the component 2 pivots relative to the bearing element 4. The element 5 comprises a substantially plate-like horseshoe shaped mounting member 18 which partially surrounds the female guide 10 and extends transversely of the longitudinal direction of the component 2. The upper side 19 of the plate-like member 18 includes a surface 20 which faces upwardly toward and is or can be contacted by the adjacent portion of the bearing element 4 on the component 1. As can be seen in FIG. 3, the mounting member 18 has an open recess or slot 21 which is bounded by a substantially U-shaped internal surface and extends from the upper side to the underside of the member 18, as considered in the longitudinal direction of the component 2. That (concave) portion 22 of the internal surface of the member 18 which bounds the innermost portion of the recess 21 is adjacent to the front portion of the abutment 12, namely to that portion of the abutment 12 which is overlapped by the abutment 13. The abutment 13 extends radially inwardly beyond the surface portion 22 and toward the guide 10. As can be seen in FIG. 3, the abutment 13 has an arcuate surface which is complementary to external surface of the adjacent portion of the guide 10.

The abutment 13 is spaced apart from the upper side 26 of a platform 25 which forms part of the bearing element 5 on the component 2. The space 27 between the underside of the abutment 13 and the upper side 26 of the platform 25 receives, with requisite clearance, the abutment 12 on the lower end portion 15 of the female guide 10. The abutment 12 can turn in the space 27 and is further free to move, within prescribed limits, up and down, as viewed in FIG. 1 or 2 (or the abutment 13 can move up and down relative to the abutment 12). The platform 25 supports the aforementioned U-shaped plate-like mounting member 18 which, in turn, carries the abutment 13. The marginal portion 28 of the upper side 26 of the platform 25 has an upwardly extending bead which extends into a complementary arcuate groove or depression in the underside 29 of the member 18. The latter is in full surface-to-surface contact with the platform 25. The front portion 30 of the member 18 is secured to the platform 26 by a fastener 31 in the form of a screw. The head of the illustrated fastener 31 is at least partially recessed into the upper side of the member 18. The rear portion 32 of the member 18 is formed with two blind bores or sockets 33, 34 whose axes register with one another and are located in the general plane of the member 18. The blind bores or sockets 33, 34 receive portions of retaining or maintaining pins which overlie the beaded portion 28 of the platform 25.

The front portion 23 of the first abutment 12 is convex (as at 24) and its curvature conforms to that of the portion 22 of the internal surface bounding the recess 21 of the mounting member 18. The reference character 16 denotes a flat which is provided on the abutment 12 opposite an upwardly facing surface 17 which is in contact with the abutment 13 in an end position of the component 2 with reference to the component 1 (as viewed in the direction of movement of the component 2 about the axis A).

The internal liner 40 of the tubular guide 10 is made of a synthetic plastic material, the same as the sheath 18 in the prosthesis which is disclosed in the parent application to which reference may be had, if necessary. The material of the mounting member 18 can be the same as that of the liner 40. The part 41 denotes a casing for the male portion 9 of the hinge 7. The other parts of the improved prosthesis can be made of a suitable metallic material.

The manner of assembling the improved prosthesis is as follows:

The component 1 is preassembled in such a way that its extension 3 is articulately connected with the male portion 9 of the first hinge 7, i.e., the male portion 9 and its female guide 10 can turn back and forth about the transverse axis A. The extensions 3 and 6 are embedded into the respective bones and the male guide 14 is introduced into the central passage of the female guide 10 so that the guides 10, 14 can turn back and forth about the axis B and are further free to move axially in the directions indicated by the arrow C. The guides 10 and 14 are assembled in such a way that the aforementioned retaining pins of the beaded portion 28 extend into the respective sockets 33, 34 and the abutment 12 on the lower end portion 15 of the guide 10 extends into the space 27 between the abutment 13 and the platform 25. In the next step, the plate-like mounting member 18 is moved downwardly into full contact with the platform 25 and is secured thereto by the fastener 31. The beaded portion 28 then extends into the complementary groove at the underside 29 of the mounting member 18.

This completes the assembly of the prosthesis. The latter enables the user to move his or her tibia by pivoting the component 2 (with the guide 10 of the hinge 7 on the component 1) about the axis A. Also, the user can turn the lower component 2 relative to the upper component 1 about the common axis B of the guides 10, 14. Finally, the user can cause the lower component 2 to move up and down relative to the upper component 1 (and/or vice versa) to the extent which is determined by the dimensions of the space 27 for the abutment 12 between the abutment 13 and the platform 25. The purpose of the stop means 11 is to ensure that the extent of downward movement of the component 2 and/or the extent of upward movement of the component 1 (as viewed in FIG. 1 or 2) is automatically limited even if the user of the prosthesis is otherwise incapable of limiting the extent of reciprocability of the components 1 and 2 relative to each other. The extent of movability of the components 1 and 2 in the directions of the arrow C can be selected in dependency on any number of parameters, such as the age of the user, the ability of the user to limit the movements of the components 1 and 2 in the direction of the axis B and/or others.

The improved stop 11 takes up stresses which develop as a result of longitudinal movement of the component 1 relative to the component 2 and/or vice versa and which cannot be taken up by the aforementioned apparatus. Moreover, the improved prosthesis allow for all such movements which are permitted by a knee joint without subjecting the connections between the extensions 3, 6 and the respective bones and/or the connections between the components 1 and 2 to excessive stresses. It has been found that the improved prosthesis can be used with particular advantage as a substitute for a knee joint. The provision of stop means 11 in an artificial knee ensures that such prosthesis can be used for long periods of time and without the danger of transmitting excessive stresses to the femur and/or tibia.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. An artificial prosthesis, particularly an internal prosthesis, comprising elongated first and second components designed to engage with the respective parts of the anatomy which are normally connected to each other by a joint, such as a knee joint, said components being reciprocable with reference to each other in the directions of elongation thereof, said first component having a first extension receivable in a femur and said second component having a second extension receivable in a tibia; stop means for limiting the extent of reciprocability of said components with reference to each other in said directions of elongation thereof; and a first hinge defining a pivot axis extending substantially transversely of the directions of elongation of said components and arranged to permit relative pivotal movements of said components about said pivot axis, said first hinge comprising a first portion on said first component and a complementary second portion having a first guide, said first guide being pivotable with said second about said pivot axis and said second component having a second guide cooperating with said first guide to define therewith a second hinge for clockwise and counterclockwise angular movement of said components relative to each other about a second axis which is at least substantially normal to said pivot axis, one of said components being reciprocable relative to the other of said components in the direction of said second axis, said stop means comprising a first abutment provided on said first component and at least partially surrounding said first guide, and a second abutment provided on said second component and arranged to engage said first abutment in response to movement of said one component in the direction of said second axis and transversely of said pivot axis, said second guide extending into said first guide and being rigid with said second component, said first guide surrounding said second guide and being coupled to said first component for movement about said pivot axis, said first guide having an end portion which is adjacent to said second component and said first abutment being provided on such end portion of said first guide.

2. The prosthesis of claim 1, wherein said first abutment extends radially of and away from said second axis.

3. The prosthesis of claim 1, wherein said first abutment has a side contacting said second abutment in a predetermined end position of said one component in which said stop means prevents further movement of said one component relative to the other component in one direction.

4. The prosthesis of claim 1, wherein said first abutment has a flat which is located at one side of said second axis and moves toward and away from said first extension in response to movement of said components about said pivot axis.

5. The prosthesis of claim 1, wherein said second component has a bearing element and further comprising means for mounting said second abutment on said bearing element.

6. The prosthesis of claim 5, wherein said mounting means comprises a substantially horseshoe-shaped member which is affixed to said bearing element and partially surrounds said first guide, said member being located in a plane which is substantially normal to said second axis and having a side facing toward said first component, said first component having a second bearing element adjacent to and movable into contact with said side of said member.

7. The prosthesis of claim 5, wherein said mounting means comprises a substantially horseshoe-shaped member which is affixed to said bearing element and has a recess bounded by a substantially U-shaped internal surface, said surface having a concave portion outwardly adjacent to said first guide.

8. The prosthesis of claim 7, wherein said first abutment includes an arcuate portion which is received in said recess and is adjacent to said second abutment, as considered in the direction of said second axis.

9. The prosthesis of claim 7, wherein said second abutment extends radially inwardly of the concave portion of said internal surface and toward said second axis.

10. The prosthesis of claim 9, wherein said second abutment is located at one end of said concave portion, as considered in the direction of said second axis.

11. The prosthesis of claim 5, wherein said first guide has a substantially cylindrical external surface and said second abutment has a concave surface which is complementary and adjacent to said external surface.

12. The prosthesis of claim 5, wherein said bearing element includes a platform having a side facing toward said first component and said first abutment is disposed between said second abutment and said side of said platform.

13. The prosthesis of claim 12, wherein said second abutment and said side of said platform define a space which receives said first abutment with limited freedom of movement in the direction of said second axis.

14. The prosthesis of claim 5, wherein said first abutment is located between said bearing element and said second abutment and has limited freedom of movement relative to said second abutment and said bearing element, as considered in the direction of said second axis.

15. The prosthesis of claim 5, wherein said bearing element comprises a platform member, a substantially plate-like mounting member disposed between said platform member and said first component and supporting said second abutment, and means for securing said members to each other.

16. The prosthesis of claim 15, wherein one of said members has a beaded portion and the other of said members has a groove snugly receiving said beaded portion.

17. The prosthesis of claim 15, wherein said members are in pronounced surface-to-surface contact with each other.

18. The prosthesis of claim 15, wherein said securing means comprises a fastener having a head which is at least partially recessed into one of said members.

19. The prosthesis of claim 15, further comprising means for releasably maintaining said members in surface-to-surface contact with each other including at least one socket provided in one of said members and a coupling element provided on the other of said members and extending into said socket.

* * * * *